United States Patent
Watanabe et al.

(10) Patent No.: US 10,829,475 B2
(45) Date of Patent: Nov. 10, 2020

(54) PRODUCTION AND PURIFICATION METHODS FOR EFINACONAZOLE

(71) Applicant: KAKEN PHARMACEUTICAL CO., LTD., Tokyo (JP)

(72) Inventors: Masahito Watanabe, Fujieda (JP); Takeshi Kanayama, Fujieda (JP)

(73) Assignee: KAKEN PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 16/795,275

(22) Filed: Feb. 19, 2020

(65) Prior Publication Data

US 2020/0181110 A1 Jun. 11, 2020

Related U.S. Application Data

(60) Division of application No. 16/438,011, filed on Jun. 11, 2019, which is a continuation of application No. PCT/JP2018/019324, filed on May 18, 2018.

(30) Foreign Application Priority Data

May 19, 2017 (JP) ................................. 2017-100248

(51) Int. Cl.
| | |
|---|---|
| C07D 401/06 | (2006.01) |
| C07D 487/10 | (2006.01) |
| C07D 401/14 | (2006.01) |
| A61P 31/10 | (2006.01) |
| A61K 31/4439 | (2006.01) |

(52) U.S. Cl.
CPC ............ *C07D 401/06* (2013.01); *A61P 31/10* (2018.01); *C07D 401/14* (2013.01); *C07D 487/10* (2013.01); *A61K 31/4439* (2013.01)

(58) Field of Classification Search
CPC .. C07D 401/06; C07D 401/14; C07D 487/10; A61P 31/10
USPC ...................................................... 546/272.4
See application file for complete search history.

(56) References Cited

U.S. PATENT DOCUMENTS

| | | | |
|---|---|---|---|
| 5,962,476 A | 10/1999 | Naito et al. | |
| 8,871,942 B2 | 10/2014 | Mimura et al. | |
| 2013/0150586 A1 | 6/2013 | Mimura et al. | |
| 2016/0376253 A1 | 12/2016 | Attolino et al. | |
| 2017/0129874 A1 | 5/2017 | Gangavaram et al. | |
| 2018/0162833 A1* | 6/2018 | Bhirud ................... | C07C 69/78 |

FOREIGN PATENT DOCUMENTS

| | | |
|---|---|---|
| CN | 104292214 A | 1/2015 |
| CN | 104327047 A | 2/2015 |
| CN | 105503826 A | 4/2016 |
| CN | 106565672 A | 4/2017 |
| CN | 106608867 A | 5/2017 |
| CN | 106810534 A | 6/2017 |
| CN | 106928186 A | 7/2017 |
| CN | 106995434 A | 8/2017 |
| EP | 0698606 A | 2/1996 |
| EP | 3091007 A1 | 11/2016 |
| IN | 4509CHE2015 A | 7/2017 |
| JP | 2017-036262 | 2/2017 |

(Continued)

OTHER PUBLICATIONS

English Translation of the Written Opinion of the International Searching Authority, International Patent Application No. PCT/JP2018/019324, dated Aug. 7, 2018, 14 pages. (Year: 2018).*

(Continued)

*Primary Examiner* — Daniel R Carcanague
(74) *Attorney, Agent, or Firm* — Hamre, Schumann, Mueller & Larson, P.C.

(57) ABSTRACT

The present invention provides efinaconazole producing and purifying methods adapted to industrial scale that provide high-purity efinaconazole in high yield by simple operations using specific impurities as indices. The efinaconazole producing method comprises:

step A of forming a toluene solution comprising compound (II), compound (III), an inorganic base, and toluene in a volume (L) which is 2 to 5 times the mass (kg) of compound (II);

step B of subjecting the toluene solution to reaction under heating;

step C of washing the reaction mixture from step B to obtain a toluene solution of crude efinaconazole in which the residual amount of 4-MP is not more than 5 wt % of efinaconazole.

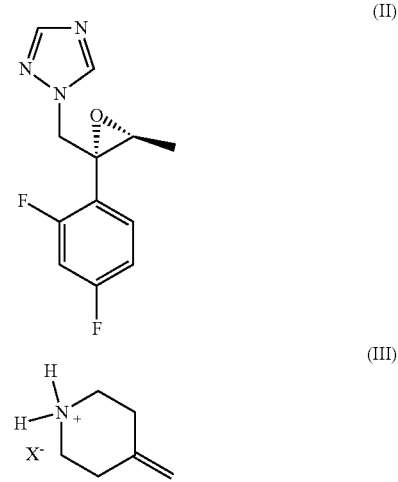

15 Claims, No Drawings

(56) References Cited

FOREIGN PATENT DOCUMENTS

| WO | 94/26734 A1 | 11/1994 |
| WO | 2012/029836 A1 | 3/2012 |
| WO | 2016/079728 A1 | 5/2016 |
| WO | 2016/116919 A1 | 7/2016 |
| WO | 2016/181306 A1 | 11/2016 |
| WO | 2016/193917 A1 | 12/2016 |
| WO | 2017114743 A1 | 7/2017 |
| WO | 2017/178909 A1 | 10/2017 |

OTHER PUBLICATIONS

Precise organic synthesis (experiment translation manual), Second revised edition, Nankodo Co., Ltd.. pp. 27-31 with translation of relevant part.
International Search Report and Written Opinion, International Patent Application No. PCT/JP2018-019324, dated Aug. 7, 2018 (16 pages) with English translation of Search Report.
Ogura; Chem. Pharm Bull. 1999, 47, 1417-1425 (Year: 1999).
Tamura; J. Org. Chem. 2014. 3272-3278. (Year: 2014).
Zhu; Org. Process Res. Dev. 2018, 22, 625-632. (Year: 2018).

\* cited by examiner

PRODUCTION AND PURIFICATION METHODS FOR EFINACONAZOLE

CROSS REFERENCE TO RELATED APPLICATIONS

The present application is a continuation application of International Application No. PCT/JP2018/019324, filed on May 18, 2018.

TECHNICAL FIELD

The present invention relates to efinaconazole producing and purifying methods adapted to industrial scale that provide high-purity efinaconazole in high yield by simple operations using specific impurities as indices.

BACKGROUND ART

Efinaconazole is a triazole compound having antifungal activity that is represented by formula (I):

[Formula 1]

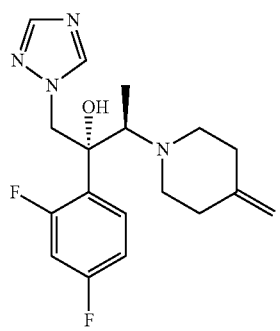

Efinaconazole is known as an active ingredient of topical therapeutics for onychomycosis and sold under different drug names, in Japan as CLENAFIN® (10% solution for topical application to nails), and in the US as JUBLIA® (10% topical solution).

Efinaconazole is produced by methods in which (2R, 3S)-2-(2,4-difluorophenyl)-3-methyl-2-[(1H-1,2,4-triazol-1-yl)methyl]oxirane (hereinafter sometimes referred to as epoxytriazole) is subjected to ring-opening addition using 4-methylenepiperidine (hereinafter sometimes referred to as 4-MP) (Patent Documents 1, 2, and 3). Also known are methods for purifying the efinaconazole obtained (Patent Documents 4 and 5).

As regards production and purification methods adapted to industrial scale, it is required to shorten the reaction time and simplify the work-up operation but the problem with these approaches is that a variety of impurities is formed or the contents of impurities are increased.

Even the following recently developed methods for producing and purifying efinaconazole are not suitable as methods for production on an industrial scale. For example, a method is known that comprises neutralizing 4-methylenepiperidine hydrochloride with potassium hydroxide, then adding lithium bromide and epoxytriazole in a toluene solution for reaction to obtain crude efinaconazole, then isolating p-toluenesulfonate of the crude efinaconazole, neutralizing the p-toluenesulfonate with potassium carbonate in a dichloromethane solution, and thereafter performing crystallization from an ethanol-water mixed solvent to purify the efinaconazole (Patent Document 6). However, because of the absence of yield data, this method cannot be referred to for the above-described purpose and it involves the problem of prolonged reaction time.

A method is known that comprises adding a strong organic base tetramethyl guanidine, 4-methylenepiperidine hydrobromide, lithium nitrate and epoxytriazole in acetonitrile for reaction to obtain crude efinaconazole, then isolating p-toluenesulfonate of the crude efinaconazole, neutralizing the p-toluenesulfonate with sodium hydroxide in a methanol-water mixed solvent and adding water for crystallization to purify the efinaconazole (Patent Document 7). This method, however, has the problem of prolonged reaction time. What is more, this method requires a cumbersome work-up operation since the crude efinaconazole is crystallized even before the p-toluenesulfonate of efinaconazole is formed.

CITATION LIST

Patent Documents

Patent Document No. 1: WO 94/26734
Patent Document No. 2: WO 2012/029836
Patent Document No. 3: WO 2016/079728
Patent Document No. 4: WO 2016/116919
Patent Document No. 5: WO 2016/181306
Patent Document No. 6: WO 2016/193917
Patent Document No. 7: United States Patent Publication No. 2016/0376253

SUMMARY OF INVENTION

Technical Problem

Prior studies of efinaconazole producing and purifying methods adapted to industrial scale involved a problem in that when the reaction time was shortened or the work-up operation was simplified, a variety of impurities is formed or the contents of impurities are increased. In addition, some impurities are difficult to determine for their presence and this has made it difficult to control the contents of impurities.

Given this background, the present invention has as its object providing efinaconazole producing and purifying methods adapted to industrial scale that can provide high-purity efinaconazole in high yield by simple operations.

Solution to Problem

In order to attain the stated object, the present inventors conducted an intensive study and found that compound (IV), compound (V), compound (VI), compound (VII), compound (VIII), compound (IX), compound (X), compound (XI), compound (XII), and compound (XIII) could occur as impurities in the process of producing efinaconazole, with the additional discovery that by using these specific impurities as indices from the viewpoints of their amounts and their removability, high-purity efinaconazole could be produced in high yield by simple operations.

Specifically, it was found that in a method comprising reacting epoxytriazole with an acid addition salt of 4-methylenepiperidine to synthesize efinaconazole (this step is hereinafter sometimes referred to as "ring-opening addition reaction"), then forming p-toluenesulfonate of the efinaconazole and isolating it, then neutralizing the p-toluenesulfonate of efinaconazole to obtain efinaconazole, the duration of ring-opening addition reaction could be shortened by using a specific solvent (toluene) in the reaction but that the impurity compound (IV) increased. The increased amount of impurity compound (IV) was difficult to be removed by conventional methods but unexpectedly, the amount of compound (IV) was found to decrease upon adjusting the pH of the aqueous layer while washing the reaction mixture after the reaction.

It was also revealed that in the case of simplifying the work-up operation subsequent to a ring-opening addition reaction using toluene as a reaction solvent, the yield of conversion to p-toluenesulfonate would decrease unless the unreacted 4-methylenepiperidine was removed by liquid-liquid separation. As regards this problem, the present inventors found that by either adjusting the pH of the aqueous layer or passing through more than one step of liquid-liquid separation while washing the reaction mixture after the ring-opening addition reaction, the amount of 4-methylenepiperidine contained in the solution which is to be subjected to conversion to p-toluenesulfonate can be rendered as small as possible, eventually resolving the problem of low yield.

The present inventors further discovered that in the step of isolating the p-toluenesulfonate of efinaconazole, it is possible to remove compound (XIII) that is so close to efinaconazole in terms of physicochemical behavior that no method has yet been established for its analysis or removal and have led to the establishment of a method for analyzing compound (XIII).

The present inventors further discovered that in the step of crystallizing efinaconazole using an ethanol-water mixed solvent, the crystals of efinaconazole was obtained in high yield by adding water after the crystals of efinaconazole has formed in the solution.

Briefly, the present invention provides the following.

[1] A method of producing efinaconazole comprising:
step A of forming a toluene solution comprising a compound represented by formula (II):

[Formula 2]

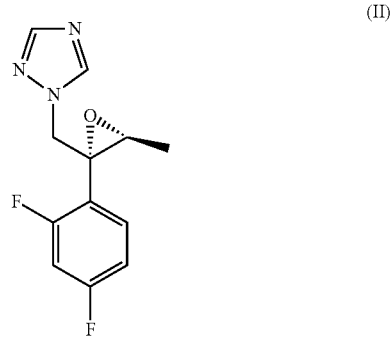

(hereinafter sometimes referred to as epoxytriazole);
a compound represented by formula (III):

[Formula 3]

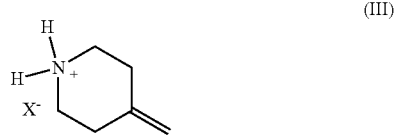

(where X is Cl, Br or I and the compound is hereinafter sometimes referred to as 4-MP·HX salt); an inorganic base, and toluene in a volume (L) which is 2 to 5 times the mass (kg) of epoxytriazole;
step B of subjecting the toluene solution to reaction under heating;
step C of washing the reaction mixture from step B, specifically washing the same more than once or washing so that the pH of the aqueous layer after the washing operation is between 3 and 5, thereby obtaining a toluene solution of crude efinaconazole in which the residual amount of 4-MP is not more than 5 wt % of efinaconazole;
step D of mixing the toluene solution of crude efinaconazole with 2-propanol and p-toluenesulfonate or a hydrate thereof to precipitate p-toluenesulfonate of efinaconazole;
step E of isolating the p-toluenesulfonate of efinaconazole;
step F of neutralizing the p-toluenesulfonate of efinaconazole.

[2] The method as recited in [1], wherein formula (III) is a compound represented by formula (III-A):

[Formula 4]

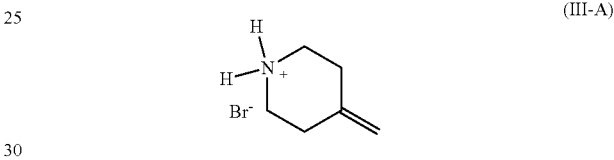

(the compound is hereinafter sometimes referred to as 4-MP·HBr salt), which is contained in an amount of 1-1.6 moles relative to one mole of epoxytriazole and wherein the inorganic base is lithium hydroxide or a hydrate thereof and contained in an amount of 1-1.6 moles relative to one mole of epoxytriazole.

[3] The method as recited in any one of [1] and [2], wherein the reaction time in step B is 1-15 hours.

[4] The method as recited in any one of [1] to [3], wherein the washing in step C is such that the pH of an aqueous layer after the washing operation is between 3 and 5, and the content of a compound represented by formula (IV):

[Formula 5]

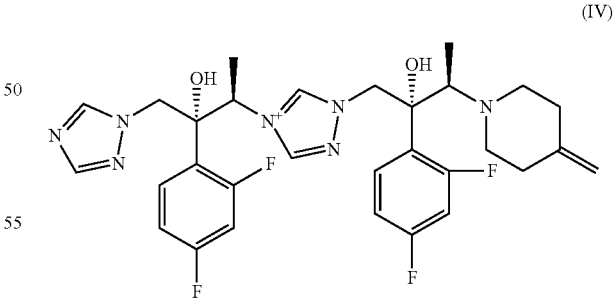

(which is hereinafter sometimes referred to as compound (IV)) in the efinaconazole as obtained after step F is no more than 0.50% (HPLC area percentage).

[5] The method as recited in any one of [1] to [4], further comprising, after step F:
step G of forming a solution of the obtained efinaconazole in an ethanol-water mixed solvent and crystallizing the efinaconazole;

step H of further adding water and isolating the efinaconazole that has precipitated out;

wherein the content of the compound represented by formula (IV) in the efinaconazole as obtained after step H is no more than 0.10% (HPLC area percentage).

[6] The method as recited in [5], wherein the solution in ethanol-water mixed solvent in step G is one that uses a 50-65% ethanol-water mixed solvent.

[7] The method as recited in either [5] or [6], wherein the amount of water to be added in step H is such that the ethanol concentration in the solution is 35-45%.

[8] The method as recited in any one of [5] to [7], wherein the content of a compound represented by formula (V):

[Formula 6]

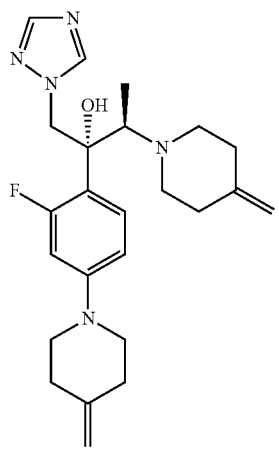

(V)

(the compound is hereinafter sometimes referred to as compound (V)) in the efinaconazole as obtained after step H is no more than 0.50% (HPLC area percentage).

[9] The method as recited in any one of [5] to [8], wherein the content of a compound represented by formula (VI):

[Formula 7]

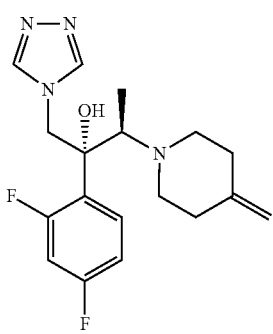

(VI)

(the compound is hereinafter sometimes referred to as compound (VI)) in the efinaconazole as obtained after step H is no more than 0.15% (HPLC area percentage).

[10] The method as recited in any one of [5] to [9], wherein the content of a compound represented by formula VII:

[Formula 8]

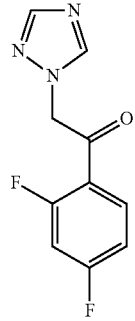

(VII)

(the compound is hereinafter sometimes referred to as compound (VII)) in the efinaconazole as obtained after step H is no more than 0.15% (HPLC area percentage).

[11] The method as recited in any one of [5] to [10], wherein the content of a compound represented by formula VIII:

[Formula 9]

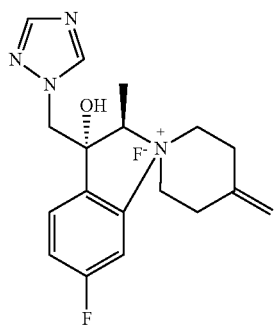

(VIII)

(the compound is hereinafter sometimes referred to as compound (VIII)) in the efinaconazole as obtained after step H is no more than 0.15% (HPLC area percentage).

[12] The method as recited in any one of [5] to [11], wherein the content of a compound represented by formula IX:

[Formula 10]

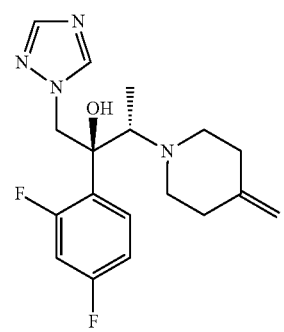

(IX)

(the compound is hereinafter sometimes referred to as compound (IX)) in the efinaconazole as obtained after step H is no more than 0.10% (HPLC area percentage).

[13] The method as recited in any one of [5] to [12], wherein the content of a compound represented by formula X:

[Formula 11]

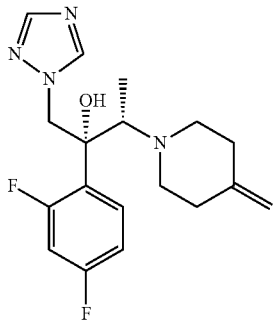

(X)

(the compound is hereinafter sometimes referred to as compound (X)) in the efinaconazole as obtained after step H is no more than 0.10% (HPLC area percentage).

[14] The method as recited in any one of [5] to [13], wherein the content of a compound represented by formula XI:

[Formula 12]

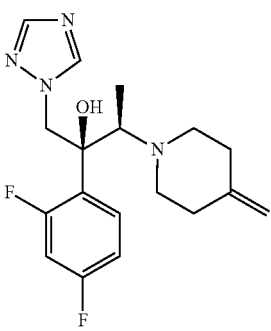

(XI)

(the compound is hereinafter sometimes referred to as compound (XI)) in the efinaconazole as obtained after step H is no more than 0.10% (HPLC area percentage).

[15] The method as recited in any one of [5] to [14], wherein the content of a compound represented by formula XII:

[Formula 13]

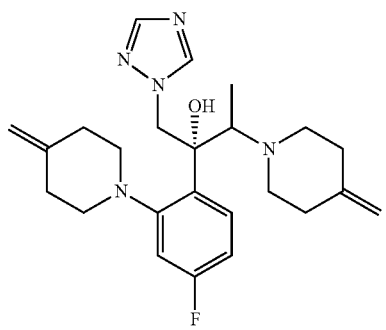

(XII)

(the compound is hereinafter sometimes referred to as compound (XII)) in the efinaconazole as obtained after step H is no more than 0.10% (HPLC area percentage).

[16] The method as recited in any one of [5] to [15], wherein the content of a compound represented by formula XIII:

[Formula 14]

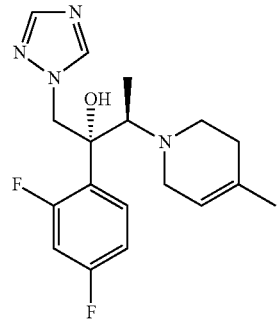

(XIII)

(the compound is hereinafter sometimes referred to as compound (XIII)) in the efinaconazole as obtained after step H is no more than 0.10% (HPLC area percentage).

[17] The method as recited in any one of [1] to [16], wherein the purity of efinaconazole is no less than 98.0% (HPLC area percentage).

[18] The method as recited in any one of [1] to [16], wherein the purity of efinaconazole is no less than 99.0% (HPLC area percentage).

[19] Compound (IV) represented by formula IV:

[Formula 5]

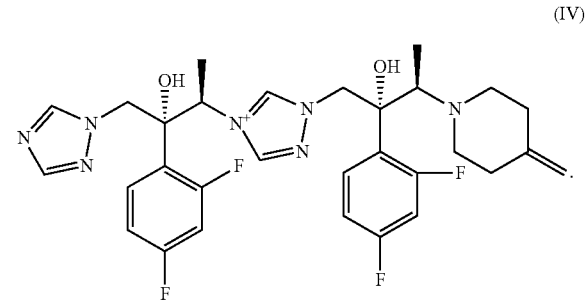 [SMILES: C=C1CCN([C@H](C)[C@](O)(Cn2c[n+]([C@H](C)[C@](O)(Cn3cncn3)c3ccc(F)cc3F)cn2)c2ccc(F)cc2F)CC1]

(IV)

[20] Compound (VI) represented by formula VI:

[Formula 7]

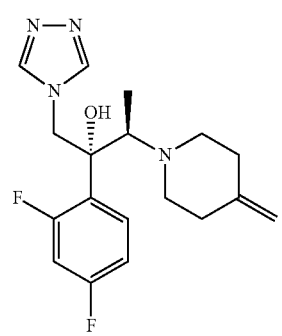

(VI)

[21] Compound (VIII) represented by formula VIII:

[Formula 9]

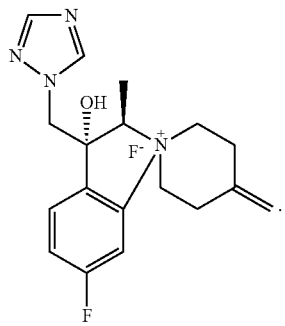

(VIII)

[22] Compound (XIII) represented by formula XIII:

[Formula 15]

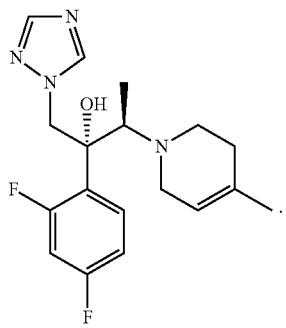

(XIII)

[23] Efinaconazole wherein the content of compound (IV) is 0.10% or less, the content of compound (V) is 0.50% or less, the content of compound (VI) is 0.15% or less, the content of compound (VII) is 0.15% or less, the content of compound (VIII) is 0.15% or less, the content of compound (IX) is 0.10% or less, the content of compound (X) is 0.10% or less, the content of compound (XI) is 0.10% or less, the content of compound (XII) is 0.10% or less, and the content of compound (XIII) is 0.10% or less, as well as the purity of efinaconazole is no less than 98.0% and each value of percentage is HPLC area percentage.

[24] Efinaconazole wherein the content of compound (IV) is 0.10% or less, the content of compound (V) is 0.15% or less, the content of compound (VI) is 0.15% or less, the content of compound (VII) is 0.15% or less, the content of compound (VIII) is 0.15% or less, the content of compound (IX) is 0.10% or less, the content of compound (X) is 0.10% or less, the content of compound (XI) is 0.10% or less, the content of compound (XII) is 0.10% or less, and the content of compound (XIII) is 0.10% or less, as well as the purity of efinaconazole is no less than 98.0% and each value of percentage is HPLC area percentage.

[25] Efinaconazole wherein the content of compound (IV) is 0.05% or less, the content of compound (V) is 0.50% or less, the content of compound (VI) is 0.05% or less, the content of compound (VII) is 0.05% or less, the content of compound (VIII) is 0.05% or less, the content of compound (IX) is 0.05% or less, the content of compound (X) is 0.05% or less, the content of compound (XI) is 0.05% or less, the content of compound (XII) is 0.05% or less, and the content of compound (XIII) is 0.05% or less, as well as the purity of efinaconazole is no less than 99.0% and each value of percentage is HPLC area percentage.

[26] Efinaconazole wherein the content of compound (IV) is 0.05% or less, the content of compound (V) is 0.15% or less, the content of compound (VI) is 0.05% or less, the content of compound (VII) is 0.05% or less, the content of compound (VIII) is 0.05% or less, the content of compound (IX) is 0.05% or less, the content of compound (X) is 0.05% or less, the content of compound (XI) is 0.05% or less, the content of compound (XII) is 0.05% or less, and the content of compound (XIII) is 0.05% or less, as well as the purity of efinaconazole is no less than 99.0% and each value of percentage is HPLC area percentage.

[27] Use of compound (IV), compound (V), compound (VI), compound (VII), compound (VIII), compound (IX), compound (X), compound (XI), compound (XII) or compound (XIII) for producing the efinaconazole as recited in any of [23] to [26].

[28] A method for measuring the purity of efinaconazole which is characterized by analyzing compound (IX) as an index for impurity by HPLC.

[29] The method as recited in [28], wherein a column packed with cellulose derivatives bonded silica gel and a mixed solvent comprising of a buffer of potassium hexafluorophosphate and acetonitrile are used in HPLC.

[30] A method for measuring the purity of efinaconazole which is characterized by analyzing compound (XIII) as an index for impurity by HPLC.

[31] The method as recited in [30], wherein a column packed with octadecylsilanized silica gel and a mixed solvent comprising of an ammonium hydrogencarbonate solution and acetonitrile are used in HPLC.

[32] A method for measuring the purity of efinaconazole which is characterized by analyzing compound (IV), compound (V), compound (VI), compound (VII), compound (VIII), compound (X), compound (XI) and compound (XII) as indices for impurities by HPLC.

[33] The method as recited in [32], wherein a column packed with octadecylsilanized silica gel and a mixed solvent comprising of water, acetonitrile and trifluoroacetic acid are used in HPLC.

[34] A method for crystalizing efinaconazole from an efinaconazole solution that uses a 50-65% ethanol-water mixed solvent, wherein after crystals of efinaconazole has formed in the solution, water is further added so that the ethanol concentration of the solution is between 35% and 45% for crystallizing the efinaconazole.

Advantageous Effects of Invention

According to the present invention, high-purity efinaconazole can be provided in high yield by simple operations adapted to industrial scale with reference made to specific impurities as indices.

DESCRIPTION OF EMBODIMENTS

Hereinbelow, steps A to H will be described in detail.

The term "toluene solution" in step A refers to a solution using toluene as the major solvent and it may be a mixed solution containing other solvents. Preferably, it is a solution containing no less than 90% of toluene, more preferably, a solution containing no less than 99% of toluene.

The amount of toluene to be used in step A is 2-5 times the mass (kg) of epoxytriazole. Due to this small amount of toluene, the reaction time in step B can be shortened.

The order in which epoxytriazole, compound (III) and an inorganic base are added to toluene is not particularly limited and they may be added simultaneously.

Symbol X in compound (III) represents Cl, Br or I, preferably Br. The equivalent amount of compound (III) is preferably 1.1-1.6 equivalents, more preferably 1.5 equivalents, per equivalent of epoxytriazole.

The "inorganic base" in step A is preferably lithium hydroxide or a hydrate thereof. The equivalent amount of the inorganic base is preferably 1.1-1.6 equivalents, more preferably 1.5 equivalents, per equivalent of epoxytriazole.

The reaction temperature in step B is not particularly limited as long as the reaction proceeds fast enough and the contents of impurities are not increased. It is preferably 60-110° C., more preferably 70-90° C.

The reaction time in step B is not particularly limited as long as the reaction proceeds and the contents of impurities are not increased. It is preferably 1-22 hours, more preferably 1-15 hours, even more preferably 1-12 hours.

"Washing" in step C is not particularly limited as long as the residual unreacted 4-MP can be removed and the recovery of the produced efinaconazole is high. Washing may be done either once or, if necessary, more than once. The residual amount of 4-MP greatly affects the yield of efinaconazole in step D and subsequent purification steps, so at the time when the work-up operation of step C ends, the residual amount of 4-MP is preferably 5 wt % or less, more preferably 2 wt % or less, of the efinaconazole in the toluene solution of crude efinaconazole.

"Washing" in step C is more preferably performed with "an acidic aqueous solution." For example, washing can be done using an acidic aqueous solution such as an aqueous solution of ammonium chloride, hydrochloric acid, an aqueous solution of phosphoric acid, or an aqueous solution of acetic acid. In one preferred embodiment, washing with hydrochloric acid, for example, may be followed by washing with an aqueous solution of acetic acid. In another preferred embodiment, washing with water may be followed by washing with an aqueous solution of ammonium chloride, then with an aqueous solution of acetic acid. The pH of the aqueous layer after the washing operation is preferably 3-8, more preferably 3-5, even more preferably 3.5-4.5. In the ring-opening addition reaction, there is formed an impurity represented by formula (IV), for example, but this can be removed into the aqueous layer by making pH adjustment to one of the ranges noted above. As a result of this work-up, the content of the impurity represented by formula (IV) is reduced to 0.5% and less at the time when step F ends.

After the washing operation in step C, the solvent may, depending on the need, be distilled off for concentration, whereupon "the toluene solution of crude efinaconazole" is obtained.

The amount of "p-toluenesulfonate or a hydrate thereof" in step D is preferably 1.0-1.2 equivalents, more preferably 1.1 equivalents, per equivalent of the crude efinaconazole.

In step D, the reaction mixture is heated and then cooled, whereupon a p-toluenesulfonate of efinaconazole is precipitated. If necessary, a mixed solvent containing water, methanol, or ethanol, etc. may be employed.

The present inventors have found that step E of isolating the p-toluenesulfonate of efinaconazole enables removal of compound (XIII) which is so close to efinaconazole in terms of physicochemical behavior that no method for its analysis or removal has yet been established.

The neutralizing agent to be used in step F is not particularly limited and may preferably be exemplified by NaHCO$_3$. The solvent to be used is not particularly limited and may preferably be exemplified by an ethyl acetate-water mixed liquid.

The ethanol-water mixed solvent to be used in step G is not particularly limited as long as efinaconazole crystallizes and the ethanol concentration is preferably 50-70%, more preferably 50-65%, even more preferably 58-62%, and most preferably 60%.

The amount of water to be added in step H is determined from the viewpoints of the yield of the objective product efinaconazole and the contents of impurities and it is preferably such that the ethanol concentration in the reaction mixture after the addition of water is 35-45%, more preferably 40%.

The percentage (%) for the contents of efinaconazole and each of the impurities as used hereinafter shall, unless otherwise indicated, refer to HPLC area percentage.

In the next place, the impurities that can be removed by the present invention are described.

Compound (IV) (1-[(2R,3R)-2-(2,4-difluorophenyl)-2-hydroxy-3-(4-methylenepiperidin-1-yl)butyl]-4-[(2'R,3'R)-2'-(2,4-difluorophenyl)-2'-hydroxy-1'-(1H-1,2,4-triazol-1-yl)butan-3'-yl]-1H-1,2,4-triazol-4-ium)

The time of ring-opening addition reaction in step B can be shortened by using toluene in a volume (L) which is 2-5 times the mass (kg) of epoxytriazole; on the other hand, this usually increases the amount of compound (IV).

The amount of compound (IV) can be reduced by the washing operation in step C of the present invention. Briefly, the content of compound (IV) decreases upon adjusting the pH of the aqueous layer in the process of washing the reaction mixture from the ring-opening addition reaction.

$^1$H-NMR (500 MHz, CDCl$_3$) δ: 0.93 (3H, d, J=6.7 Hz), 1.45 (3H, d, J=6.7 Hz), 2.27-2.46 (6H, m), 2.73 (2H, m), 3.17 (1H, q, J=6.7 Hz), 4.33 (1H, d, J=14.3 Hz), 4.62 (2H, s), 4.89 (1H, d, J=14.3 Hz), 5.16 (1H, d, J=14.3 Hz), 5.37 (1H, d, J=14.3 Hz), 5.60 (1H, q, J=6.7 Hz), 6.01 (1H, br s), 6.70-6.83 (4H, m), 7.14 (1H, br s), 7.43-7.52 (2H, m), 7.76 (1H, s), 8.02 (1H, s), 8.53 (1H, s), 11.00 (1H, s).

Compound (VI) ((2R,3R)-2-(2,4-difluorophenyl)-3-(4-methylenepiperidin-1-yl)-1-(4H-1,3,4-triazol-4-yl)butan-2-ol)

Compound (VI) is mainly removed in step H.

$^1$H-NMR (400 MHz, CDCl$_3$) δ: 1.07 (3H, dd, J=4.8, 7.1 Hz), 2.14-2.40 (8H, m), 2.75 (1H, q, J=7.3 Hz), 4.28 (1H, dd, J=1.4, 14.2 Hz), 4.66 (2H, s), 4.69 (1H, dd, J=1.4, 14.2 Hz), 6.23 (1H, br s), 6.73-6.87 (2H, m), 7.50-7.58 (1H, m), 8.15 (2H, s).

Compound (VIII) ((2'R,3'R)-3'-hydroxy-2'-methyl-4-methylene-3'-(1H-1,2,4-triazol-1-yl)methyl-1-azoniaspiro[cyclohexane-1,1'-(6'-fluoroindane)]fluoride)

Compound (VIII) is mainly removed in step C.

$^1$H-NMR (400 MHz, DMSO-d$_6$) δ: 1.61 (3H, d, J=6.6 Hz), 2.46-2.93 (4H, m), 3.42-3.58 (1H, m), 3.72-3.76 (1H, m), 4.12-4.20 (1H, m), 4.60 (1H, d, J=14.5 Hz), 4.71-4.73 (2H, m), 4.94 (1H, s), 4.99 (1H, s), 5.16 (1H, d, J=14.5 Hz), 7.45-7.52 (1H, m), 7.70-7.75 (1H, m), 7.91-8.00 (1H, m), 8.02 (1H, s), 8.74 (1H, s).

Compound (XIII) ((2R,3R)-2-(2,4-difluorophenyl)-3-[4-methyl-5,6-dihydropyridin-1(2H)-yl]-1-(1H-1,2,4-triazol-1-yl)butan-2-ol)

Compound (XIII) is so close to efinaconazole in physicochemical behavior that no method for its analysis or removal has yet been established. The present invention enables the removal of compound (XIII), thereby enabling the production of high-purity efinaconazole. Compound (XIII) is mainly removed in step E.

¹H-NMR (500 MHz, CDCl₃) δ: 1.00 (3H, dd, J=6.9, 2.8 Hz), 1.67 (3H,s), 1.88 (1H, m), 2.08 (1H, m), 2.31 (1H, m), 2.70 (1H, m), 2.87-2.92 (2H, m), 3.13 (1H, m), 4.77 (1H, d, J=14.6 Hz), 4.86 (1H, d, J=14.4 Hz), 5.32 (1H, s), 5.53 (1H, br s), 6.72-6.81 (2H, m), 7.52 (1H, dt, J=6.6, 9.0 Hz), 7.78 (1H, s), 8.03 (1H, s).

Described next is the method established by the present invention for measuring the purity of efinaconazole.

The method for measuring the purity of efinaconazole in accordance with the present invention is characterized by analyzing compound (IX) as an index of impurity. Specifically, the method uses a column packed with cellulose derivatives bonded silica gel in HPLC analysis.

The mobile phase is preferably a mixed solvent comprising of a potassium hexafluorophosphate buffer and acetonitrile which are preferably mixed at a ratio in the range of 90-10:10-90, more preferably in the range of 70-60:30-40, even more preferably in the range of 64-61:36-39. Depending on the need, the gradient method may be adopted and in that case, a mixed solvent with a mixing ratio in one of the ranges set forth above may be used in at least part of the method. The pH of the potassium hexafluorophosphate buffer is preferably 7 or less, more preferably in the range of 1.8-3.0, and even more preferably in the range of 1.9-2.1. The salt concentration of the potassium hexafluorophosphate buffer is preferably between 0.05 mol/L and 0.5 mol/L, more preferably 0.1-0.4 mol/L, and even more preferably 0.25-0.35 mol/L.

By means of the present method, compound (IX) and efinaconazole are separated appropriately so that the purity of efinaconazole and the content of compound (IX) can be measured.

In another embodiment of the present invention, the method for measuring the purity of efinaconazole is characterized by analyzing compound (XIII) as an index of impurity. Specifically, the method uses a column packed with octadecylsilanized silica gel in HPLC analysis.

The mobile phase is preferably a mixed solvent comprising of an ammonium hydrogencarbonate aqueous solution and acetonitrile which are preferably mixed at a ratio in the range of 90-10:10-90, more preferably in the range of 70-15:30-85, even more preferably in the range of 60-45:40-55, and particularly preferably in the range of 55-51:45-49. Depending on the need, the gradient method may be adopted and in that case, a mixed solvent with a mixing ratio in one of the ranges set forth above may be used in at least part of the method. The salt concentration of the ammonium hydrogencarbonate aqueous solution is preferably between 0.001 mol/L and 0.05 mol/L, more preferably 0.005-0.015 mol/L.

By means of the present method, compound (XIII) and efinaconazole are separated appropriately so that the purity of efinaconazole and the content of compound (XIII) can be measured.

In yet another embodiment of the present invention, the method for measuring the purity of efinaconazole is characterized by analyzing compound (IV), compound (V), compound (VI), compound (VII), compound (VIII), compound (X), compound (XI) and compound (XII) as indices of impurities. Specifically, the method uses a column packed with octadecylsilanized silica gel in HPLC analysis.

The mobile phase is preferably a water/acetonitrile mixed solvent to which is added trifluoroacetic acid, with the mixing ratio being preferably in the range of 90-10:10-90, more preferably in the range of 90-50:10-50, even more preferably in the range of 85-50:15-50. The trifluoroacetic acid added preferably accounts for 0.01% to 0.5% of the mobile phase. Depending on the need, the gradient method may be adopted and in that case, a mixed solvent with a mixing ratio in one of the ranges set forth above may be used in at least part of the method.

By means of the present method, compound (IV), compound (V), compound (VI), compound (VII), compound (VIII), compound (X), compound (XI) and compound (XII) are appropriately separated from efinaconazole so that the purity of efinaconazole and the contents of those impurity compounds can be measured.

EXAMPLES

On the pages that follow, the present invention will be described more specifically by means of working examples, to which the present invention is by no means limited.

Reference Example (The Production Method Using Acetonitrile as a Reaction Solvent)

Epoxytriazole (20.00 g, 0.080 mol), 4-MP·HBr salt (21.26 g, 0.119 mol), lithium hydroxide (2.86 g, 0.119 mol) and acetonitrile (80 mL) were mixed and heated under reflux for 16 hours. After cooling the reaction mixture, ethanol (80 mL) and water (120 mL) were added. After cooling to 5° C. and below, seed crystals of efinaconazole were added and the mixture was stirred for crystallization. After adding water (360 mL) and stirring the mixture at room temperature, the resulting crystals were filtered and dried to obtain crude efinaconazole (yield: 22.49 g, 81%).

Crude efinaconazole (20.00 g, 0.057 mol), p-toluenesulfonate monohydrate (12.01 g, 0.063 mol) and 2-propanol (381 mL) were mixed and heated to form a solution. The solution was cooled to 5° C. or below for crystallization. The crystals obtained were filtered and dried to obtain p-toluenesulfonate of efinaconazole (yield: 27.54 g, 92%).

The p-toluenesulfonate of efinaconazole (25.00 g, 0.048 mol), ethyl acetate (250 mL), water (250 mL) and sodium hydrogencarbonate (4.44 g, 0.053 mol) were mixed and neutralized. After removing the aqueous layer by liquid-liquid separation, the organic layer was washed twice with an aqueous sodium chloride solution and dried over sodium sulfate (82.25 g). After filtering off the sodium sulfate, the filtrate was concentrated under reduced pressure. To the residue, ethanol (81 mL) and water (53 mL) were added and the mixture was heated to form a solution. The solution was cooled and seed crystals of efinaconazole were added for crystallization. After cooling to 5° C. and below, the resulting crystals were filtered and dried to obtain efinaconazole (yield: 13.12 g, 78%).

Example 1A (Using Toluene as a Reaction Solvent in Steps A to C and Evaluating the Reaction Time in Step B)

To a mixture of epoxytriazole (20.00 g, 0.080 mol), 4-MP·HBr salt (21.26 g, 0.119 mol) and lithium hydroxide (2.86 g, 0.119 mol), toluene (80 mL) was mixed, followed by stirring at 80° C. The conversion ratio was followed up in terms of HPLC area percentage measured by high-performance liquid chromatography.

TABLE 1

| Reaction time | Efinaconazole | Residual epoxytriazole | Compound (IV) |
|---|---|---|---|
| 4 hrs | 77.99% | 17.83% | 3.76% |
| 6 hrs | 86.17% | 9.25% | 4.29% |

TABLE 1-continued

| Reaction time | Efinaconazole | Residual epoxytriazole | Compound (IV) |
|---|---|---|---|
| 10 hrs | 91.04% | 3.31% | 4.45% |
| Reference Example Acetonitrile as solvent (reaction time: 14 hrs) | 80.86% | 10.80% | 0.99% |

As it turned out, when toluene was used as a reaction solvent in steps A to C, the reaction time was considerably shortened, the residual amount of the starting material epoxytriazole was reduced and the yield of efinaconazole was improved as compared with the data for the Reference Example in the table. On the other hand, the amount of the impurity compound (IV) formed was greater than in the Reference Example.

Example 1B (The Residual Amount of 4-MP at the Time when Step C (The Work-Up Operation After Ring-Opening Addition Reaction) Ended and the Effect of Residual 4-MP in Subsequent Steps)

Toluene solutions of crude efinaconazole containing different contents of 4-MP were prepared and each of these toluene solutions was mixed with 2-propanol and p-toluenesulfonate (PTSA) monohydrate (1.1 eq.), followed by precipitating a p-toluenesulfonate of efinaconazole, which was isolated to calculate the yield of efinaconazole.

To calculate the weight of 4-MP in the toluene solutions of crude efinaconazole, a test was conducted by gas chromatography under the conditions set out below and quantification was performed by the absolute calibration curve method.

Test Conditions
Detector: Hydrogen flame ionization detector
Column: A fused silica tube 0.32 mm in internal diameter and 30 m in length, coated with 5% phenyl/95% dimethylpolysiloxane for gas chromatography of 1.00 μm thickness.
Column temperature: Maintain at 80° C. for 10 min, then increase gradually to 250° C. at the rate of 25° C. per minute and maintain at 250° C. for 5 minutes.
Injection temperature: A constant temperature of about 250° C.
Detector temperature: A constant temperature of about 290° C.
Carrier gas: Helium
Flow rate: About 33 cm/sec
Split ratio: 1:25
Injection volume: 1 μL
Preparation of sample solutions: Toluene solutions of crude efinaconazole were dissolved in t-butyl methyl ether to prepare 1 mg/mL solutions which were used as the sample solutions.

TABLE 2

| No. | HPLC purity of efinaconazole in the toluene solutions of crude efinaconazole | 4-MP* contained in the toluene solutions of crude efinaconazole | Yield** of p-toluenesulfonate of efinaconazole at the end of step E |
|---|---|---|---|
| 1 | 91.49% | 12.0 wt % | 43% |
| 2 | 94.30% | 7.4 wt % | 74% |
| 3 | 92.94% | 4.5 wt % | 84% |

TABLE 2-continued

| No. | HPLC purity of efinaconazole in the toluene solutions of crude efinaconazole | 4-MP* contained in the toluene solutions of crude efinaconazole | Yield** of p-toluenesulfonate of efinaconazole at the end of step E |
|---|---|---|---|
| 4 | 91.36% | 1.9 wt % | 92% |
| 5 | 92.44% | Not detected | 89% |

*Weight (g) of 4-MP/Weight (g) of efinaconazole
**(Weight (g) of p-toluenesulfonate of efinaconazole × 348.39)/(Net content (g) of efinaconazole in the toluene solution of crude efinaconazole × 520.59)

It was revealed that the yield of p-toluenesulfonate of efinaconazole was markedly affected by the amount of 4-MP remained in the toluene solutions of crude efinaconazole. The amount of 4-MP is preferably 5 wt % or less, more preferably 2 wt % or less, of efinaconazole.

Example 1C (Evaluating the Removal of Compound (IV) with an Acidic Aqueous Solution in Step C (The Work-Up Operation After Ring-Opening Addition Reaction))

The reaction mixture prepared in Example 1A (reaction time: 10 hours) was cooled and mixed with hydrochloric acid for adjusting the pH of the aqueous layer to 6.8; thereafter, the aqueous layer 1 was removed to obtain an organic layer 1. The organic layer 1 was washed with an aqueous solution of acetic acid or phosphoric acid at different concentrations so that the pH of the aqueous layer would vary, whereupon an organic layer 2 and an aqueous layer 2 were obtained. The organic layer 2 and the aqueous layer 2 were analyzed by high-performance liquid chromatography to calculate the HPLC area percentage of compound (IV) and the amount of efinaconazole loss into the aqueous layer 2.

TABLE 3

| pH of aqueous layer 2 | HPLC relative area percentage of compound (IV) in organic layer 2 | Amount of efinaconazole loss* into aqueous layer 2 |
|---|---|---|
| Before washing | 4.43% (organic layer 1) | — |
| 7.9 | 4.44% | 0.0 wt % |
| 5.0 | 4.03% | 0.1 wt % |
| 4.2 | 2.51% | 0.4 wt % |
| 3.5 | 1.21% | 2.8 wt % |
| 3.3 | 0.93% | 11.4 wt % |
| 2.3 | Not detected | 48.7 wt % |

*Amount (g) of efinaconazole in aqueous layer 2/Amount (g) of efinaconazole in organic layer 1

The study revealed that when the pH of the aqueous layer after the washing operation was 3-5, preferably at 3.5-4.5, efinaconazole was hardly lost whereas the impurity compound (IV) could be considerably reduced in amount.

Example 2

Epoxytriazole (1.0 kg, 3.98 mol), 4-MP·HBr salt (1.06 kg, 5.95 mol), lithium hydroxide (143 g, 5.97 mol) and toluene (2 L) were mixed and stirred at 95-105° C. for 5.8 hours. The reaction mixture was cooled and mixed with water. The aqueous layer was removed and the organic layer was successively washed with an aqueous solution of ammonium chloride and an aqueous sodium chloride solution to obtain a toluene solution of crude efinaconazole.

The toluene solution of crude efinaconazole (in the indicated entire amount), p-toluenesulfonate monohydrate (757 g, 3.98 mol) and 2-propanol (13 L) were mixed and heated to form a solution. The solution was cooled to 5° C. or below for crystallization. The resulting crystals were filtered and dried to obtain a p-toluenesulfonate of efinaconazole (yield: 1.8 kg, 87% (in 2 steps)).

The p-toluenesulfonate of efinaconazole (0.9 kg, 1.73 mol), ethyl acetate (9 L), water (9 L) and sodium hydrogencarbonate (160 g, 1.90 mol) were mixed and neutralized. After removing the aqueous layer by liquid-liquid separation, the organic layer was washed with an aqueous sodium chloride solution to obtain an organic layer. This procedure was repeated using the same amounts of the p-toluenesulfonate of efinaconazole and the resulting organic layers were combined. The combined organic layers were concentrated under reduced pressure and, ethanol (5.8 L) and water (3.8 L) were added to the residue, followed by heating to form a solution. The solution was cooled and seed crystals of efinaconazole (as prepared by the method of the Reference Example) were added for crystallization. After cooling to 5° C. or below, the resulting crystals were filtered and dried to obtain efinaconazole (yield: 962 g, 80%).

Example 3

The p-toluenesulfonate of efinaconazole (6.00 g, 0.0115 mol), ethyl acetate (60 mL), water (60 mL) and sodium hydrogencarbonate (1.07 g, 0.0127 mol) were mixed and neutralized. After removing the aqueous layer by liquid-liquid separation, the organic layer was washed twice with an aqueous sodium chloride solution and dried over sodium sulfate (19.74 g). After filtering off the sodium sulfate, the filtrate was concentrated under reduced pressure. To the residue, ethanol (19 mL) and water (13 mL) were added, followed by heating to form a solution. The solution was cooled and seed crystals of efinaconazole were added for crystallization. After cooling to 5° C. or below, water (16 mL) was added. The resulting crystals were filtered and dried to obtain efinaconazole (yield: 3.76 g, 94%).

Example 4

Epoxytriazole (100 g, 0.398 mol), 4-MP·HBr salt (106.4 g, 0.598 mol), lithium hydroxide (14.3 g, 0.597 mol) and toluene (400 mL) were mixed and stirred at 80° C. for 11.5 hours. The reaction mixture was cooled and mixed with hydrochloric acid to adjust the pH of the aqueous layer to 6.0. The aqueous layer was removed and the organic layer was successively washed with an aqueous solution of acetic acid (the pH of the aqueous layer after the washing was 4.3) and water (the pH of the aqueous layer after the washing was 4.6). The resulting solution was concentrated to obtain a toluene solution of crude efinaconazole (238.87 g, net content of efinaconazole: 124.6 g, yield: 90%).

A toluene solution of crude efinaconazole (95.83 g, net content of efinaconazole: 50.0 g, 0.144 mol), p-toluenesulfonate monohydrate (30.03 g, 0.158 mol), 2-propanol (600 mL) and water (2.5 g) were mixed and heated to form a solution. The solution was cooled to 5° C. or below for crystallization. The resulting crystals were filtered to obtain p-toluenesulfonate of efinaconazole as wet crystals (yield: 88.14 g, net content of p-toluenesulfonate of efinaconazole: 69.81 g, yield: 93%).

The p-toluenesulfonate of efinaconazole as wet crystals (80.0 g, net content of p-toluenesulfonate of efinaconazole: 63.36 g, 0.122 mol), ethyl acetate (441 mL), water (441 mL) and sodium hydrogencarbonate (11.16 g, 0.133 mol) were mixed and neutralized. After removing the aqueous layer by liquid-liquid separation, the organic layer was washed with water to obtain an organic layer. The organic layer was concentrated under reduced pressure and to the residue, ethanol (205 mL) and water (137 mL) were added, followed by heating to form a solution. The solution was cooled and seed crystals of efinaconazole were added for crystallization. After cooling to 5° C. or below, water (170 mL) was added. The resulting crystals were filtered and dried to obtain efinaconazole (yield: 40.31 g or 95%).

TEST EXAMPLES

The purity and impurity contents data for the respective Examples were obtained by the following methods of analysis.

Test Example 1 (Analysis Method: to Analyze Compound (IV), Compound (V), Compound (VI), Compound (VII), Compound (VIII), Compound (X), Compound (XI), and Compound (XII))

The contents of compound (IV), compound (V), compound (VI), compound (VII), compound (VIII), compound (X), compound (XI) and compound (XII) were determined by a method based on high-performance liquid chromatography (HPLC).

Efinaconazole as obtained in the Reference Example and in Examples 2 to 4 was dissolved in methanol to prepare 1 mg/mL solutions, which were used as sample solutions. A 15 µL portion of each sample solution was tested by liquid chromatography under the following conditions and the respective peak areas were measured by automatic integration.

Test Conditions
Detector: UV absorption photometer (measurement wavelength: 262 nm)
Column: A stainless steel column 4.6 mm in inside diameter and 15 cm in length, packed with 5 µm in particle diameter of octadecylsilanized silica gel for liquid chromatography.
Column temperature: A constant temperature of about 40° C.
Mobile phase A: A mixture of water/trifluoroacetic acid (1000:1)
Mobile phase B: A mixture of acetonitrile/trifluoroacetic acid (1000:1)
Flow of mobile phases: Gradient was controlled by mixing the mobile phases A and B as directed in Table 4.

TABLE 4

| Time after injection of samples (min) | Mobile phase A (vol %) | Mobile phase B (vol %) |
| --- | --- | --- |
| 0~15 | 85 → 50 | 15 → 50 |

Flow rate: About 1 mL per minute
Time span of measurement: 15 minutes (excluding the solvent peak)

Test Example 2 (Analysis Method: to Analyze Compound (XIII))

The content of compound (XIII) was determined by a method based on high-performance liquid chromatography (HPLC).

Efinaconazole as obtained in the Reference Example and in Examples 2 to 4 was dissolved in a dissolving solution to prepare 10 mg/mL solutions, which were used as sample solutions. A 15 µL portion of each sample solution was tested by liquid chromatography under the following conditions and the respective peak areas were measured by automatic integration.

Dissolving solution: A mixture of 0.05 mol/L ammonium hydrogencarbonate aqueous solution/acetonitrile (53:47)

Test Conditions

Detector: UV absorption photometer (measurement wavelength: 262 nm)

Column: A stainless steel column 4.6 mm in inside diameter and 15 cm in length, packed with 3 μm in particle diameter of octadecylsilanized silica gel for liquid chromatography.

Column temperature: A constant temperature of about 40° C.

Mobile phase A: 0.01 mol/L ammonium hydrogencarbonate aqueous solution

Mobile phase B: Acetonitrile

Flow of mobile phases: Gradient was controlled by mixing the mobile phases A and B as directed in Table 5.

TABLE 5

| Time after injection of samples (min) | Mobile phase A (vol %) | Mobile phase B (vol %) |
|---|---|---|
| 0~30 | 53 | 47 |
| 30~50 | 53→20 | 47→80 |

Flow rate: About 1 mL per minute

Time span of measurement: 50 minutes (excluding the solvent peak)

Test Example 3 (Analysis Method: to Analyze Compound (IX))

The content of compound (IX) was determined by a method based on high-performance liquid chromatography (HPLC).

Efinaconazole as obtained in the Reference Example and in Examples 2 to 4 was dissolved in a dissolving solution to prepare 15 mg/mL solutions, which were used as sample solutions. A 10 μL portion of each sample solution was tested by liquid chromatography under the following conditions and the respective peak areas were measured by automatic integration.

Dissolving solution: A mixture of 0.3 mol/L potassium hexafluorophosphate buffer (pH 2.0)/acetonitrile (1:1)

Test Conditions

Detector: UV absorption photometer (measurement wavelength: 262 nm)

Column: A stainless steel column 4.6 mm in inside diameter and 15 cm in length, packed with 5 μm in particle diameter of cellulose derivatives bonded silica gel for liquid chromatography (silica gel coated with cellulose derivatives)

Column temperature: A constant temperature of about 25° C.

Mobile phase: A mixture of 0.3 mol/L potassium hexafluorophosphate buffer (pH 2.0)/acetonitrile (63:37)

Flow rate: About 0.5 mL per minute

Time span of measurement: 30 minutes (excluding the solvent peak)

The contents of efinaconazole and impurities observed in the respective Examples by the analysis methods described above were as shown below (HPLC area percentage).

TABLE 6

|  | Reference Example | Example 2 | Example 3 | Example 4 |
|---|---|---|---|---|
| Efinaconazole* | 99.93% | 99.99% | 99.88% | 99.99% |
| Compound (IV) | Not detected | Not detected | Not detected | Not detected |
| Compound (V) | 0.06% | Not detected | 0.11% | Not detected |
| Compound (VI) | Not detected | Not detected | Not detected | Not detected |
| Compound (VII) | Not detected | Not detected | Not detected | Not detected |
| Compound (VIII) | Not detected | Not detected | Not detected | Not detected |
| Compound (IX)** | Not detected | Not detected | Not detected | Not detected |
| Compound (X) | Not detected | Not detected | Not detected | Not detected |
| Compound (XI) | Not detected | Not detected | Not detected | Not detected |
| Compound (XII) | Not detected | Not detected | Not detected | Not detected |
| Compound (XIII)*** | 0.01% | 0.01% | 0.01% | 0.01% |
| Others | Not detected | Not detected | Not detected | Not detected |

*The difference between 100% and the total sum of the impurities (%) was taken.
**Measured by the analysis method of Test Example 3.
***Measured by the analysis method of Test Example 2.

As seen from the foregoing results, the method of the present invention for producing efinaconazole can provide high-purity efinaconazole in high yield by simple operations.

INDUSTRIAL APPLICABILITY

According to the present invention, high-purity efinaconazole can be provided in high yield by simple operations using specific impurities as indices, with the result that there can be provided methods for producing and purifying efinaconazole that are adapted to industrial scale.

The invention claimed is:

1. A method of producing efinaconazole comprising:
 (A) forming a primary toluene solution comprising:
  a compound represented by formula (II):

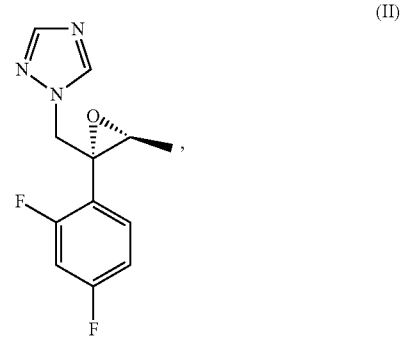

hereinafter sometimes referred to as epoxytriazole;

a compound represented by formula (III):

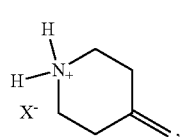

(III)

where X is Cl, Br or I, and the compound (III) is hereinafter sometimes referred to as 4-MP·HX salt, which is a HX salt of 4-MP;

an inorganic base; and toluene in a volume (L), which is from 2 to 5 times mass (kg) of the epoxytriazole;

(B) subjecting the primary toluene solution to a reaction under heating;

(C) washing the resulting reaction mixture from (B), which is:

(C)-(i) washing the resulting reaction mixture from (B) more than once, or (C)-(ii) washing the resulting reaction mixture from (B) so that pH of an aqueous layer after the washing of the reaction mixture is in a range from 3 to 5, thereby obtaining a secondary toluene solution of crude efinaconazole in which a residual amount of the 4-MP is not more than 5 wt % of efinaconazole;

(D) mixing the secondary toluene solution of crude efinaconazole with 2-propanol and p-toluenesulfonate or a hydrate thereof so as to precipitate p-toluenesulfonate of efinaconazole;

(E) isolating the precipitated p-toluenesulfonate of efinaconazole; and (F) neutralizing the isolated p-toluenesulfonate of efinaconazole.

2. The method according to claim 1, wherein the compound (III) is a compound represented by formula (III-A):

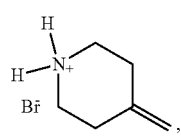

(III-A)

where the compound (III-A) is hereinafter sometimes referred to as 4-MP·HBr salt, wherein the compound (III-A) is contained in an amount in a range from 1 to 1.6 moles relative to one mole of the epoxytriazole, and the inorganic base is lithium hydroxide or a hydrate thereof and contained in an amount in a range from 1 to 1.6 moles relative to one mole of the epoxytriazole.

3. The method according to claim 1, wherein a reaction time in (B) is in a range from 1 to 15 hours.

4. The method according to claim 1, wherein the washing (C)-(ii) is performed as the washing (C), and a content of a compound represented by formula (IV):

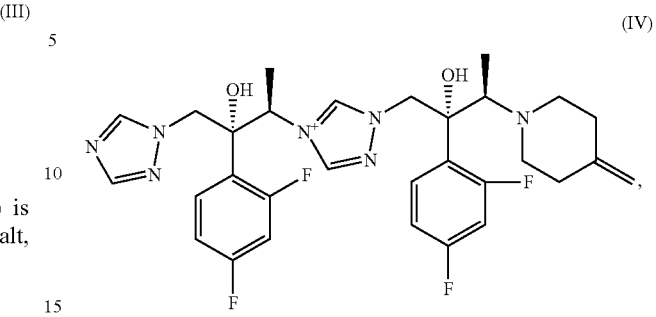

(IV)

in the efinaconazole as obtained by (F) is no more than 0.50% as a HPLC area percentage detected with UV light at a wavelength of 262 nm, wherein a column packed with octadecylsilanized silica gel and a mixed solvent comprising water, acetonitrile, and trifluoroacetic acid are used in HPLC.

5. The method according to claim 1, further comprising, after (F):

(G) forming a solution of the obtained efinaconazole in an ethanol-water mixed solvent and crystallizing the efinaconazole; and (H) further adding water to the ethanol-water mixed solvent solution from (G) and isolating the efinaconazole that has precipitated out, wherein a content of a compound represented by formula (IV):

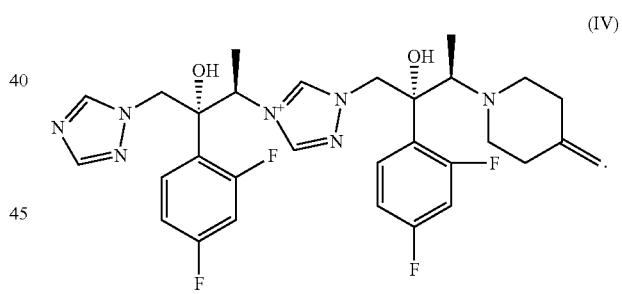

(IV)

in the obtained efinaconazole is no more than 0.10% as a HPLC area percentage detected with UV light at a wavelength of 262 nm, wherein a column packed with octadecylsilanized silica gel and a mixed solvent comprising water, acetonitrile, and trifluoroacetic acid are used in HPLC.

6. The method according to claim 5, wherein the solution of the ethanol-water mixed solvent in (G) is a solution in which ethanol is mixed with water in a range from 50 to 65% by volume-relative to the solution.

7. The method according to claim 5, wherein an amount of the water added to the solution of the ethanol-water mixed solvent in (H) is such that an ethanol concentration in the resulting solution after the adding of the water is in a range of 35-45% by volume relative to the resulting solution.

8. The method according to claim 5, wherein a content of a compound represented by formula (V):

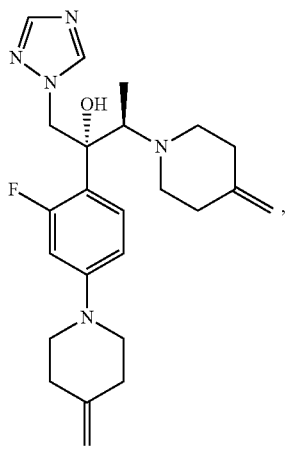

(V)

hereinafter sometimes referred to as compound (V), in the obtained efinaconazole is no more than 0.50% as a HPLC area percentage detected with UV light at a wavelength of 262 nm, wherein a column packed with octadecylsilanized silica gel and a mixed solvent comprising water, acetonitrile, and trifluoroacetic acid are used in HPLC.

9. The method according to claim 8, wherein the content of the compound (V) in the obtained efinaconazole is no more than 0.15% as the HPLC area percentage.

10. The method according to claim 5, wherein a content of a compound represented by formula (XIII):

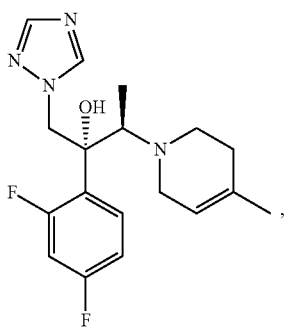

(XIII)

hereinafter sometimes referred to as compound (XIII), in the obtained efinaconazole is no more than 0.10% as a HPLC area percentage detected with UV light at a wavelength of 262 nm, wherein a column packed with octadecylsilanized silica gel and a mixed solvent comprising an ammonium hydrogencarbonate solution and acetonitrile are used in HPLC.

11. The method according to claim 10, wherein the content of the compound (XIII) in the obtained efinaconazole is no more than 0.05% as the HPLC area percentage.

12. The method according to claim 10, wherein a content of a compound represented by formula (V):

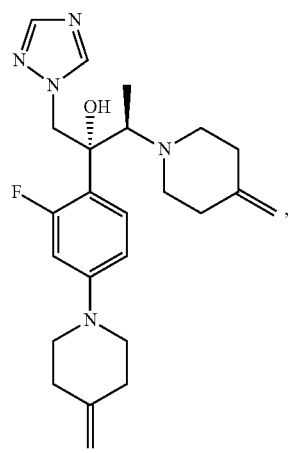

(V)

hereinafter sometimes referred to as compound (V), in the obtained efinaconazole is no more than 0.15% as a HPLC area percentage detected with UV light at a wavelength of 262 nm, wherein a column packed with octadecylsilanized silica gel and a mixed solvent comprising water, acetonitrile, and trifluoroacetic acid are used in HPLC, and wherein the content of the compound (XIII) in the obtained efinaconazole is no more than 0.05% as the HPLC area percentage.

13. The method according to claim 12, wherein purity of the obtained efinaconazole is no less than 98.0% as a HPLC area percentage detected with UV light at a wavelength of 262 nm.

14. The method according to claim 12, wherein purity of the obtained efinaconazole is no less than 99.0% as a HPLC area percentage detected with UV light at a wavelength of 262 nm.

15. The method according to claim 5, wherein the obtained efinaconazole has purity of 99.99% or more as a HPLC area percentage detected with UV light at a wavelength of 262 nm.

* * * * *